United States Patent
Hill (10) Patent No.: US 10,220,008 B2
(45) Date of Patent: Mar. 5, 2019

(54) TREATMENT AND PREVENTION OF STROKE AND OTHER NEUROLOGICAL DISORDERS

(71) Applicant: STC.UNM, Albuquerque, NM (US)

(72) Inventor: Jeff Wade Hill, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 99 days.

(21) Appl. No.: 14/911,943

(22) PCT Filed: Aug. 14, 2014

(86) PCT No.: PCT/US2014/051025
§ 371 (c)(1),
(2) Date: Feb. 12, 2016

(87) PCT Pub. No.: WO2015/023830
PCT Pub. Date: Feb. 19, 2015

(65) Prior Publication Data
US 2016/0193161 A1   Jul. 7, 2016

Related U.S. Application Data

(60) Provisional application No. 61/865,733, filed on Aug. 14, 2013, provisional application No. 61/876,537, filed on Sep. 11, 2013.

(51) Int. Cl.
| | | |
|---|---|---|
| *A61K 31/138* | (2006.01) | |
| *A61K 9/00* | (2006.01) | |
| *A61K 31/27* | (2006.01) | |
| *A61K 31/325* | (2006.01) | |
| *A61K 45/06* | (2006.01) | |
| *G01N 33/50* | (2006.01) | |

(52) U.S. Cl.
CPC .......... *A61K 31/138* (2013.01); *A61K 9/0019* (2013.01); *A61K 31/27* (2013.01); *A61K 31/325* (2013.01); *A61K 45/06* (2013.01); *G01N 33/5058* (2013.01)

(58) Field of Classification Search
CPC .................................................. A61K 31/138
See application file for complete search history.

(56) References Cited

U.S. PATENT DOCUMENTS

| | | | |
|---|---|---|---|
| 5,108,901 A | 4/1992 | Anderson et al. | |
| 5,262,170 A | 11/1993 | Anderson et al. | |
| 5,411,871 A | 5/1995 | Anderson et al. | |
| 5,520,911 A | 5/1996 | Anderson et al. | |
| 5,520,913 A | 5/1996 | Anderson et al. | |
| 5,612,029 A | 3/1997 | Bennett et al. | |
| 5,616,486 A | 4/1997 | Anderson et al. | |
| 5,714,145 A | 2/1998 | Anderson et al. | |
| 5,728,567 A | 3/1998 | Anderson et al. | |
| 5,736,134 A | 4/1998 | Heyneker et al. | |
| 5,770,425 A | 6/1998 | Anderson et al. | |
| 5,770,426 A | 6/1998 | Anderson et al. | |
| 5,840,564 A | 11/1998 | Anderson et al. | |
| 7,618,615 B2 | 11/2009 | Frey, II et al. | |
| 8,518,390 B2 | 8/2013 | Kramer et al. | |
| 2004/0176347 A1 | 9/2004 | Honjo et al. | |
| 2006/0067927 A1 | 3/2006 | Chandrasekaran et al. | |
| 2007/0123556 A1 | 5/2007 | Pennypacker et al. | |
| 2008/0139614 A1 | 6/2008 | Seabrook et al. | |
| 2009/0221540 A1 | 9/2009 | Bennink | |
| 2012/0003180 A1 | 1/2012 | Bix | |
| 2012/0164157 A1 | 6/2012 | Kuebler | |
| 2014/0080873 A1 | 3/2014 | Cohen et al. | |

FOREIGN PATENT DOCUMENTS

WO     2012176172 A2     12/2012

OTHER PUBLICATIONS

Dhrymiotis et al., Effect of a vasodilator, isoxsuprine, on cerebral ischemic episodes, 1962, Current Therapeutic Research, vol. 4, No. 4, pp. 124-129 (Year: 1962).*
Taussky et al., Medical therapy for ischemic stroke: Review of intravenous and intra-arterial treatment options, 2011, World Neurosurgery, 76(65), pp. S9-S15 (Year: 2011).*
Small DL, et al.; Current and Experimental Treatment of Stroke. published in Neuropsychopharmacology: The Fifth Generation of Progress. Edited by Davis et al. American College of Neuropharmacology 2002, pp. 1327-1338.
Go As., Mozaffarian D, Roger Vl, et al. American Heart Association Statistics Committee and Stroke Statistics Subcommittee. Heart disease and stroke statistics—2013 update: a report from the American Heart Association. Circulation. 2013:127:e6-e245.
Eissa A, Kress I, Bajorek Bv, Optimizing the management of acute ischaemic stroke: a review of the utilization of intravenous recombinant tissue plasminogen activator (tPA). J Clin Pharm Ther. 2012;37:620-9.
Chong. Cr, Sullivan Dj Jr. New uses for old drugs. Nature. 2007;448:645-6.
Allison M. NCATS launches drug repurposing program. Nat Biotechnol, 2012;30:571-572.
Wang Jk, Portbury S, Thomas Mb, Barney S, Ricca Dj, Morris Dl, Warner Ds, Lo Dc, Cardiac glycosides provide neuroprotection against ischemic stroke: discovery by a brain slice-based compound screening platform. Proc Natl Acad Sci US A. 2006;103;10461-6.
Hill Jw, Poddar R, Thompson Jf, Rosenberg Ga, Yang Y, Intranuclear matrix metalloproteinases promote DNA damage and apoptosis induced by oxygen-glucose deprivation in neurons. Neuroscience. 2012;220:277-90.

(Continued)

*Primary Examiner* — Kortney L. Klinkel
*Assistant Examiner* — Tori Strong
(74) *Attorney, Agent, or Firm* — Henry D. Coleman; R. Neil Sudol (57) ABSTRACT

Using high-throughput screening, in an oxygen-glucose deprivation (OGD) model, isoxsuprine hydrochloride was identified as a potent neuroprotective compound. In an animal middle artery occlusion (MCAO) model of transient focal ischemia, isoxsuprine significantly reduced infarct volume compared to vehicle. The invention, therefore, provides methods of treatment and pharmaceutical compositions that are useful in the treatment and prevention of a wide-variety of ischemia-related injuries, including stroke.

11 Claims, 3 Drawing Sheets

(56) References Cited

OTHER PUBLICATIONS

Semkova I, Schilling M, Henrich-Noack P, Rami A, Krieglstein J, Clenbuterol protects mouse cerebral cortex and rat hippocampus from ischemic damage and attenuates glutamate neurotoxicity in cultured hippocampal neurons by induction of NGF. Brain Res. 1996;717:44-54.

Culmsee C, Semkova I, Krieglstein J. NGF mediates the neuroprotective effect the beta2-adrenoceptor agonist clenbuterol in vitro and in vivo: evidence from an NGF-antisense study. Neurochem Int. 1999;35:47-57.

Junker V, Becker A, Hühne R, Zembatov M, Ravati A, Culmsee C, Krieglstein J. Stimulation of beta-adrenoceptors activates astrocytes and provides neuroprotection. Eur J Pharmacol. 2002;446:25-36.

Savitz Sl, Erhardt Ja, Anthony Jv, Gupta G, Li X, Barone Fc, Rosenbaum Dm, The novel beta-blocker, carvedilol, provides neuroprotection in transient focal stroke. J Cereb Blood FlowMetab. 2000;20:1197-204.

Amory Dw, Grigore A, Amory Jk, Gerhardt Ma, White Wd, Smith Pk, Schwinn Da, Raves Jg, Newman Mf, Neuroprotection is associated with beta-adrenergic receptor antagonists during cardiac surgery: evidence from 2,575 patients. J Cardiothorac Vase Anesth, 2002;16;270-7.

Goyagi T, Kimura T, Nishikawa T, Tobe Y, Masaki Y, Beta-adrenoreceptor antagonists attenuate brain injury after transient focal ischemia in rats. Anesth Analg. 2006;103:658-63.

Zhu Wz, Zheng M, Koch Wj, Lefkowitz Rj, Kobilka Bk, Xiao Rp, Dual modulation of cell survival and cell death by beta(2)-adrenergic signaling in adult mouse cardiac myocytes. Proc Natl Acad Sci US A. 2001;98:1607-12.

Medina-Franco Jl, Giulianotti Ma, Welmaker Gs, Houghten Ra, Shifting from the single to the multitarget paradigm in drug discovery. Drug Discov Today, 2013;18:495-501.

Elliott J, Soydan J, Characterisation of beta-adrenoceptors in equine digital veins: implications of the modes of vasodilatory action of isoxsuprine. Equine Vet J Suppl. 1995;19:101-7.

Belloli C, Carcano R, Arioli F, Beretta C, Affinity of isoxsuprine for adrenoreceptors in equine digital artery and implications for vasodilatory action, Equine Vet J. 2000;32:119-24.

Markus T, Hansson Sr, Cronberg T, Cilio C, Wieloch T, Ley D. l3-Adrenoceptor activation depresses brain inflammation and is neuroprotective in lipopolysaccharide-induced sensitization to oxygen-glucose deprivation in organotypic hippocampal slices. J Neuroinflammation. 2010;7:94.

De PaolaM, Buanne P, Biordi L, Bertini R, Ghezzi P, Mennini T, Chemokine MIP~2/CXCL2, acting on CXCR2, induces motor neuron death in primary cultures. Neuroimmunomodulation. 2007;14:310-6.

Thirurnangalakudi L, Yin L, Rao Hv, Grammes P, IL-8 induces expression of matrixmetalloproteinases, cell cycle and pro-apoptotic proteins, and cell death in cultured neurons. J Alzheimers Dis, 2007; 11:305-11.

Zhu Y, Prehn Jh, Culmsee C, Krieglstein J, The beta2-adrenoceptor agonist clenbuterol modulates Bcl-2, Bcl-ax and Bax protein expression following transient forebrain ischemia, Neuroscience, 1999;90:1255-63.

Rami A, Volkmann T, Agarwal R, Schoninger S, Numberger F, Saido Tc, Winckler J, beta2-Adrenergic receptor responsiveness of the calpain-calpastatin system and attenuation of neuronal death in rat hippocampus after transient global ischemia, Neurosci Res. 2003; 47:373-82.

Whittemore Er, Ilyin Vt, Woodward Rm, Subtype-selectivere antagonism of NMDA receptors by Nylidrin, Soc Neurosci Abat. 1996;22:506-507.

\* cited by examiner

TREATMENT AND PREVENTION OF STROKE AND OTHER NEUROLOGICAL DISORDERS

CROSS-REFERENCE TO RELATED APPLICATIONS

This application is a United States national phase patent application based upon international patent application no. PCT/US2014/051025 filed Aug. 14, 2014, which claims priority from U.S. Provisional Patent Application Ser. No. 61/865,733, filed Aug. 14, 2013, and U.S. Provisional Patent Application Ser. No. 61/876,537, filed Sep. 11, 2013, both of which are entitled "Isoxsuprine Hydrochloride for the Treatment of Stroke and Other Neurological Disorders". The complete content of each of these applications is hereby incorporated by reference herein in its entirety.

GOVERNMENT INTEREST

To date, the invention described and claimed herein has not been developed using federal funding.

FIELD OF THE INVENTION

The invention provides methods of treatment and pharmaceutical compositions that are ssuseful in the treatment and prevention of a wide-variety of ischemia-related injuries, including stroke. Related screening assays and methods are also provided.

BACKGROUND OF THE INVENTION

On average, every 40 seconds, someone in the United States has a stroke and every 4 minutes someone dies from a stroke.[1] Stroke accounted for 1 of every 19 deaths in 2009 and, when considered separately from other cardiovascular diseases, ranks no. 4 among all causes of death.[1] Accordingly, there is much interest in therapeutic intervention to decrease neurological damage and prevent death after stroke. Despite the prevalence of stroke, currently, the only FDA-approved drug for the treatment of stroke is the thrombolytic agent, recombinant tissue plasminogen activator (tPA).[2] Although it provides neuroprotection, rtPA use is severely limited by the need to use the drug within 4.5 hours after stroke to be effective. Even if used within the therapeutic window, tPA has a risk of symptomatic intracerebral hemorrhage.[2] New treatment options are critically needed to extend the therapeutic window for thrombolysis and to provide neuroprotection to slow cell death after stroke.

Currently, it takes an average of 15 years and $800 million dollars to bring a new drug to market.[3] Each year, the FDA approves 20-30 new drugs for human use. At that rate, it will take approximately 300 years for the number of drugs currently in use to double. The repurposing of existing drugs for novel applications represents a more fruitful approach to drug discovery than the discovery of a new drug. The use of high-throughput screening for the repurposing of characterized agents with a history of human use is an important part of the National Center for Advancing Translational Sciences roadmap to enhance the path from drug to patient.[4]

To date, a single high-throughput screen for novel stroke drugs has been reported.[5] In that study, organotypic rat brain slices were used to evaluate the effects of small molecules on neuronal survival in an OGD stroke model. The study identified neriifolin, a cardiac glycoside, as a candidate stroke drug in the OGD model and confirmed in vivo functionality of the molecule in an animal model of stroke.

SUMMARY OF THE INVENTION

We report the identification of isoxsuprine and chlorphenesin as potent neuroprotectant agents against ischemia and a variety of other neurological disorders via cell-based high-throughput screening and confirmation of their functionality in transient ischemic injury in animals.

For example, using high-throughput screening of 1,200 small molecules in an oxygen-glucose deprivation (OGD) model of stroke in primary neurons, we identified isoxsuprine hydrochloride as a potent neuroprotective compound. Isoxsuprine, a $\beta$2-adrenergic agonist and vasodilator, demonstrated no loss of efficacy when administered up to an hour after reoxygenation in our in vitro stroke model. In an animal middle cerebral artery occlusion (MCAO) model of transient focal ischemia, isoxsuprine significantly reduced infarct volume compared to vehicle alone (137±18 versus 279±25 mm$^3$, p<0.001). Our results illustrate the utility of cell-based stroke models in high-throughput screening of chemical libraries for novel stroke drugs and demonstrate the significant and novel neuroprotective action of isoxsuprine hydrochloride in both in vitro and in vivo stroke models. Isoxsuprine is a neuroprotective therapeutic for the prevention of neuronal death and excitotoxicity in stroke and neurological disorders.

Our results illustrate the utility of cell-based stroke models in high-throughput screening of chemical libraries for surprising low doses of novel stroke drugs and demonstrate the significant and novel neuroprotective action of isoxsuprine (e.g. isoxsuprine hydrochloride (ISO)), chlorphenesin (e.g. chlorphenesin carbamate (CHL)) and analogs and derivatives thereof. For example, the neuroprotective function of ISO and CHL were demonstrated in both in vitro and in vivo stroke models and were shown to be useful in the prevention of neuronal death and excitotoxicity in the treatment of stroke and other neurological disorders described herein.

In one embodiment, the invention provides a method of treating or preventing an ischemic or hemorrhagic stoke or transient ischemic attack (TIA) comprising administering to a subject in need thereof an effective amount within a range from about 0.001 to about 1 mg/kg of isoxsuprine, about 0.001 to about 0.75 mg/kg of isoxsuprine, often about 0.001 to about 0.5 mg/kg of isoxsuprine, often about 0.001 to about 0.25 mg/kg of isoxsuprine, often about 0.001 to about 0.1 mg/kg (including about 0.01 to about 0.1 mg/kg within this range) or a pharmaceutically acceptable salt, analog or derivative thereof. In a preferred embodiment, the subject is administered one or more compositions selected from the group consisting of isoxsuprine hydrochloride (ISO), the 2-methanesulfonamido derivative of isoxsuprine and isoxsuprine di-TMS derivative.

In certain embodiments, isoxsuprine or a pharmaceutically acceptable salt, analog or derivative thereof is administered initially to the subject within about 15 to 30 minutes up to about 12 hours, often about 30 minutes to about 6 hours, about sixty to about one hundred twenty minutes after the subject expresses one or more symptoms of a stroke or TIA and is thereafter administered at about every sixty to about ninety minutes for about six hours or until the subject is asymptomatic (which may be more or less than six hours). Preferably, isoxsuprine or a pharmaceutically acceptable salt, analog or derivative thereof is administered intravenously.

In another embodiment, isoxsuprine or a pharmaceutically acceptable salt, analog or derivative thereof is administered to the subject intravenously at about 15 to 30 minutes up to about 12 hours, often around sixty to around one hundred twenty minutes after the subject expresses an occlusion of a cerebral artery. Isoxsuprine or a pharmaceutically acceptable salt, analog or derivative thereof may also be administered to the subject intravenously within about fifteen to about thirty minutes up to about 12 hours after the onset of reperfusion of an occluded cerebral artery. In certain embodiments, isoxsuprine or a pharmaceutically acceptable salt, analog or derivative thereof is administered intravenously at the onset of reperfusion of an occluded cerebral artery.

Our invention also provides a method of treating or preventing an ischemic or hemorrhagic stoke or transient ischemic attack (TIA) comprising administering to a subject in need thereof a therapeutically effective amount of chlorphenesin or a pharmaceutically acceptable salt, analog or derivative thereof. Preferably, the subject is administered one or more compositions selected from the group consisting of chlorphenesin carbamate (CHL), chlorphenesin succinate and chlorphenesin alkali salts. In treatment regimens involving the administration of chlorphenesin or a pharmaceutically acceptable salt, analog or derivative thereof, the same clinical protocols described above for isoxsuprine apply. For example, chlorphenesin or a pharmaceutically acceptable salt, analog or derivative thereof may be administered within about sixty to about one hundred twenty minutes after the subject expresses one or more symptoms of a stroke or TIA and thereafter may be administered at about every sixty to about ninety minutes for about six hours or until the subject is asymptomatic. Or chlorphenesin or a pharmaceutically acceptable salt, analog or derivative thereof may be administered intravenously at the onset of reperfusion of an occluded cerebral artery.

Our invention also includes methods of protecting neuronal cells from ischemia- or hypoxia-induced cell death comprising administering to a subject in need thereof a therapeutically effective amount of at least composition selected from the group consisting of isoxsuprine, chlorphenesin and the pharmaceutically acceptable salts, analogs and derivatives thereof. The subject requiring neuronal cell protection may be at risk of suffering, or may be suffering from, or may have suffered an ischemic or hemorrhagic stoke, a transient ischemic attack (TIA), head trauma, a brain hemorrhage, cardiac arrest, cerebral edema, hydrocephalus, asphyxia, thrombosis, embolism, thromboembolism, atherosclerosis, prolonged severe hypotension, intrauterine hypoxia, birth hypoxia, cardiac surgery complications or neurosurgery complications.

In the stroke and TIA treatments described herein, a subject may be treated concomitantly with one or more additional therapeutic agents or therapies as explained in detail hereinafter. For example, a subject who is suffering from, or who is at risk of developing an ischemic or hemorrhagic stoke or a transient ischemic attack may be treated isoxsuprine and/or chlorphenesin as well as an additional therapeutic agent selected from the group consisting of a thrombolytic agent, an anti-inflammatory agent, an immunosuppressant, an antioxidant, an α- or β-adrenergic agonist or antagonist and a NMDA receptor antagonist.

In another embodiment, the invention provides a method of treating or preventing a neurological disorder comprising administering to a subject in need thereof a therapeutically effective amount of at least one composition selected from the group consisting of isoxsuprine, chlorphenesin and the pharmaceutically acceptable salts, analogs and derivatives thereof, wherein the neurological disorder is selected from the group consisting of Alzheimer's disease, Parkinson's disease, Parkinsonism, Huntington's disease, Binswanger's disease, vascular cognitive impairment, vascular dementia, amyotrophic lateral sclerosis or multiple sclerosis, glaucoma, light-induced retinal degeneration or macular degeneration, retinitis pigmentosa, HIV-associated dementia (acquired immunodeficiency syndrome dementia complex) and HIV-associated neuropathy, encephalitis, causalgia or peripheral neuropathies, olivopontocerebellar atrophy, mitochondrial abnormalities, MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy, hepatic encephalopathy, Tourette's syndrome, drug addiction and drug dependency, drug withdrawal, depression and anxiety syndromes.

In still another embodiment, the invention provides a pharmaceutical composition which is useful in protecting neuronal cells from ischemia- or hypoxia-induced cell death and which comprises:
(a) a therapeutically effective amount of isoxsuprine or a pharmaceutically acceptable salt, analog or derivative thereof;
(b) a therapeutically effective amount of chlorphenesin or a pharmaceutically acceptable salt, analog or derivative thereof; and, optionally,
(c) a pharmaceutically-acceptable excipient.

In still another embodiment, the invention provides a cell-based high-throughput oxygen-glucose deprivation (OGD) screening assay for the identification of compounds that are effective in protecting neuronal cells from ischemia or hypoxia-induced cell death and which comprises a population of embryonic neuronal cells. Preferably, the embryonic neuronal cells are pure embryonic neuronal cells.

In still another embodiment, the invention provides a method of identifying compounds that are effective in protecting neuronal cells from ischemia or hypoxia-induced cell death comprising:
(a) screening one or more compounds in a high-throughput, oxygen-glucose deprivation (OGD) screening assay comprised of embryonic neuronal cells and identifying as potentially neuroprotective those of the one or more compounds that are effective in protecting the neuronal cells from ischemia or hypoxia-induced cell death; and thereafter confirming that the compound is neuroprotective by
(b) either (1) re-screening the potentially neuroprotective compound(s) in the cell-based assay after reoxygenation of the neuronal cells, or (2) screening the potentially neuroprotective compound(s) in an ischemic animal which is undergoing reperfusion.

These and other aspects of our invention are discussed further in the Detailed Description of the Invention.

BRIEF DESCRIPTION OF THE FIGURES

FIG. 2. A. Dose response of compounds administered at reoxygenation after 2 hours OGD. Optimal doses were 1 nM for isoxsuprine hydrochloride (ISO) and etilifrine hydrochloride (ETI) and 200 µM for chlorphenesin carbamate (CHL). Isoxsuprine and etilifrine were significantly more protective at 1 nM compared to 0.1 nM (*, p<0.001). Chlorphenesin carbamate was significantly more neuroprotective at 200 µM compared to 150 µM (*, p<0.05). B. Time course of administration of compounds at the optimal dose at 0, 15, 30, and 60 minutes after reoxygenation onset. Isoxsuprine and chlorphenesin carbamate demonstrated no decrease in neuroprotection when administered up to 60 minutes after reoxygenation onset. Neuroprotection by etilifrine significantly decreased when administered at 60 minutes versus time 0 (*, p<0.01).

DETAILED DESCRIPTION OF THE INVENTION

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

"Neurological disorders" or "neurodegenerative disorders" include acute and chronic conditions, disorders or diseases of the central or peripheral nervous system. A neurological disorder may be the result of injury or trauma or a disease or disorder. Acute neurological disorders include conditions involving neuronal cell death or compromised cerebrovascular insufficiency, e.g. cerebral ischemia or infarction (e.g. embolic occlusion and thrombotic occlusion), reperfusion following acute ischemia, perinatal hypoxic-ischemic injury, cardiac arrest, intracranial hemorrhage (e.g. epidural, subdural, subarachnoid and intracerebral), and intracranial and intravertebral lesions (e.g. contusion, penetration, shear, compression and laceration). As also explained in U.S. Pat. No. 8,518,390, "chronic neurodegenerative conditions include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia), demyelination diseases and disorders including multiple sclerosis and hereditary diseases such as leukodystrophies. Neurodegenerative conditions include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia."

Other neurodegenerative conditions include various neuropathies, such as multifocal neuropathies, sensory neuropathies, motor neuropathies, sensory-motor neuropathies, infection-related neuropathies, autonomic neuropathies, sensory-autonomic neuropathies, demyelinating neuropathies (including, but not limited to, Guillain-Barre syndrome and chronic inflammatory demyelinating polyradiculoneuropathy), other inflammatory and immune neuropathies, neuropathies induced by drugs, neuropathies induced by pharmacological treatments, neuropathies induced by toxins, traumatic neuropathies (including, but not limited to, compression, crush, laceration and segmentation neuropathies), metabolic neuropathies, endocrine and paraneoplastic neuropathies, among others.

The term stroke refers to any condition arising from a disruption, decrease, or stoppage of blood or oxygen flow to any part of the brain. "Ischemic stroke" refers to a stroke resulting from any disruption, decrease or stoppage in the blood supply to any part of the brain caused by any constriction or obstruction of the vasculature. The obstruction of vasculature may be either temporal or permanent. "Hemorrhagic stroke" refers to a stroke resulting from any rupture in any of the vasculature of the brain. Examples of acute neurodegenerative disorders that include stroke or involve etiology or symptoms such as those observed with stroke are listed above, and include: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), as well as whiplash and shaken infant syndrome.

"Ischemia" and its consequences are explained further in U.S. Patent Application Document No. 20140080873 as follows.

"Ischemia is a condition in which there is insufficient blood flow to a given part of the body to meet metabolic demand. This shortage of oxygen, glucose and other nutrients leads to tissue damage at the ischemic area. It can affect an entire organ, a limb or just a tissue part, depending of the vascular system involved. There are various types of ischemia with specific mechanisms, depending on the area experiencing the ischemic insult but they all share overall processes responsible for such an insult with globally common consequences.

Many events can lead to an insufficient blood supply to a given tissue: atherosclerosis, thromboembolism, hypoglycemia, tachycardia, hypotension, outside compression of a blood vessel (e.g. by a tumor or following a trauma), embolism, sickle cell disease, localized extreme cold, tourniquet application, arteriovenous malformations, peripheral artery occlusive disease, hemorrhage.

One major consequence of ischemia is the lack of oxygen normally supplied through binding to hemoglobin in red blood cells. The affected tissue rapidly becomes hypoxic if not anoxic. This, added to the lack of glucose, the energy supply, leads to the release of proteolytic enzymes, reactive oxygen species and inflammatory mediators. This so called ischemic cascade will ultimately cause cell death and tissue damage. Ischemia can thus develop in any part of the body, such as the limb, intestine, heart or brain. The heart and brain are among the organs that are the most quickly damaged by ischemia: necrosis becomes irreversible after only about 3-4 minutes after onset.

Cerebral ischemia is ischemia of the brain tissues resulting in loss of brain cells. Unlike other tissue which can survive extended periods of hypoxia, brain tissue is particularly sensitive to deprivation of oxygen or energy. Permanent damage to neurons can occur even during very brief periods of hypoxia or ischemia. At present, there is no effective neuroprotective strategy for the treatment of cerebral ischemia or hypoxia. Cerebrovascular disease is the 3rd cause of deaths worldwide (WHO 2008), being responsible for 10.8% of worldwide deaths. In addition, it is one of the first causes of long-term disability in Western countries, with more than 50% of patients being left with a motor disability and a significant loss of quality-adjusted life years (QALY). The risk of cerebral ischemia increasing with age, the burden of cerebral ischemia is becoming greater as the population is aging. The improvement of health care by the development of fast and more effective therapy would therefore have an important medical and socio-economical impact worldwide and is greatly needed.

Symptoms of cerebral ischemia and their severity vary greatly depending on the cerebral region(s) being affected. For instance, they may include weakness in one entire side of the body, impairments in speech or vision or/and mental confusion. Focal cerebral ischemia, which occurs when a blood clot has occluded a cerebral vessel and is confined to a specific region of the brain, is usually caused by thrombosis or embolism. Global cerebral ischemia, which occurs when blood flow to the entire brain is stopped or drastically reduced, is commonly caused by cardiovascular disease. The area(s) of brain tissue affected as well as the delay in diagnosis and treatment are essential factors determining the outcome of cerebral ischemia, that is to say survival and the levels of disability after recovery.

One major consequence of cerebral ischemia is neuronal damage, which is mediated by the ischemic cascade that results in tissue damage leading to subsequent neuronal death and to disruption of the blood brain barrier. It is estimated that 2 million brain cells die every minute after ischemic stroke onset. In addition, restoration of blood flow after a period of ischemia can actually be more damaging than the ischemia itself. The so called reperfusion injury can result in acceleration of neuronal death."

Thus, in certain embodiments, the methods described herein are used to treat cerebral ischemia; a de-myelinating condition; mechanical injury; hypoxia-ischemia (stroke); head and spinal cord injury; epilepsy; schizophrenia; neurodegenerative disorders such as Alzheimer's disease, Parkinson's disease, Parkinsonism; Huntington's disease, Binswanger's disease, vascular cognitive impairment, vascular dementia, amyotrophic lateral sclerosis or multiple sclerosis; glaucoma, light-induced retinal degeneration or macular degeneration; retinitis pigmentosa; HIV-associated dementia (acquired immunodeficiency syndrome dementia complex) and HIV-associated neuropathy; metabolic, mitochondrial; encephalitis; causalgia or peripheral neuropathies; olivopontocerebellar atrophy; mitochondrial abnormalities; MELAS syndrome; MERRF; Leber's disease; Wernicke's encephalopathy; Rett syndrome; homocysteinuria; hyperhomocysteinemia; hyperprolinemia; nonketotic hyperglycinemia; hydroxybutyric aminoaciduria; sulfite oxidase deficiency; combined systems disease; lead encephalopathy; hepatic encephalopathy; Tourette's syndrome; drug addiction and drug dependency; drug withdrawal; depression or anxiety syndromes.

In certain other embodiments, the methods described herein are used to treat Alzheimer's Dementia (AD), amyotrophic lateral sclerosis, depression, epilepsy, Huntington's Disease, multiple sclerosis, the neurological complications of AIDS, spinal cord injury, glaucoma and Parkinson's disease.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used for an appropriate effective period within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application. Generally, an effective amount falls within the range from about 0.001 to about 1.0 mg/kg of isoxsuprine or chlorphenesin, 0.001 to about 0.75 mg/kg of isoxsuprine or chlorphenesin, often about 0.001 to about 0.5 mg/kg, often about 0.001 to about 0.25 mg/kg, often about 0.001 to about 0.1 mg/kg (including about 0.01 to about 0.1 mg/kg within this range).

The term "compound" is used herein to describe any specific compound or bioactive agent disclosed herein, including any and all stereoisomers (including diasteromers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

The term "isoxsuprine" shall mean the compound 4-{1-hydroxy-2-[(1-methyl-2-phenoxyethyl)amino]propyl}phenol as a mixture of enantiomers and/or stereoisomers. Other names for isoxsuprine include Vasodilian and Duvadilan. Isoxsuprine as used herein often refers to a mixture of (−) erythro-isoxsuprine (αS, βR, γR) ((−) isoxsuprine) and (+)erythro-isoxsuprine (αR, βS, γS) ((+) isoxsuprine) including a racemic (isomeric) mixture of these compounds. In certain aspects of the invention, the isoxsuprine used is an isomerically enriched (−) isoxsuprine or (+) isoxsuprine compound which is at least 90% free of the other isomer, including 90, 91, 92, 93, 94, 95, 96, 97, 98, 99, 99.5 or 99.9+% free of the other isomer (an enriched isoxsuprine). In certain instances, the isomer used is substantially pure (at least 95% free) or completely free (at a level which is undetectable) from the other isomer (pure). The chemical structures of (−) isoxsuprine and (+) isoxsuprine are indicated below.

(−)erythro-isoxsuprine (+)erythro-isoxsuprine

The term "bioactive agent" refers to any biologically active compound or drug which may be formulated for use in the present invention. Exemplary bioactive agents include the compounds according to the present invention which are used to inhibit autophagy and to treat cancer as well as other compounds or agents which are otherwise described herein.

The terms "treat", "treating", and "treatment", are used synonymously to refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment, principally of cancer. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, in the case of cancer.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention.

Stroke treatment as described herein can include co-administration of one or more additional therapeutic agents selected from the group consisting of "aspirin, intercellular adhesion molecule (ICAM)-1 and LFA-1 antagonists including antibodies such as enlimomab (an anti-ICAM-1 monoclonal antibody), and anti-CD18 and anti-CD11a antibodies, human anti-leukocytic antibodies such as Hu23F2G, glycoprotein IIb IIIa antagonists such as eptifibatide (INTEGRELIN®) (an intravenous cyclical heptapeptide that selectively blocks the platelet glycoprotein IIb/IIIa receptor), direct thrombin inhibitors, external or local ultrasound, mechanical clot retrieval or inaceration, fibrinolytic agents, neuronal wound healing agents such as basic fibroblast growth factor (e.g., FIBLAST®), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenyloin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod (preferably intravenous, a fibrinogen-lowering agent derived from the venom of the Malayan pit viper), streptokinase (e.g., SAKSTAR®), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic-related neuroprotective activities, recombinant *desmodus rotundus* salivary plasminogen activator (rDSPA) alpha-1 (Schering/Teijin Pharmaceuticals), a mutant fibrin-activated human plasminogen (BB10153; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, an astrocyte-function-improving agent such as that disclosed in US 2004/0176347, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzene-disulfonate disodium n oxide), ebselen, glutathione peroxidase, norphenazone, rovelizurnab, lactacystin beta-lactone, tsukubaenolide, 4 phosphonomethylpipecolic acid, eliprodil, antibodies to ganglioside GM1, and biologically active variants, salts, and derivatives of any of the above", as well as "thrombolytic agents" e.g. streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al., (eds): Hemostasis and Thrombosis Lippincott, Philadelphia (1987) p. 886), tPA, and biologically active variants of each of the above. Suitable thrombolytic agents that may be used in this invention are disclosed, for example, in U.S. Pat. Nos. 5,770,425; 5,770,426; 5,612,029; 5,520,911; 5,736, 134; 5,728,567; 5,714,145; 5,840,564; 5,616,486; 5,411, 871; 5,520,913; 5,262,170; and 5,108,901." See U.S. Patent Application Document No. 20120164157.

Pharmaceutical Compositions

Compounds according to the present invention may be readily formulated into pharmaceutical compositions, useful in the treatment or prevention of a neurological disorder in a biological system. Pharmaceutical compositions comprise an effective amount of one or more compounds according to the present invention in combination with a pharmaceutically acceptable carrier, additive or excipient, optionally in combination with at least one additional agent, in the case of cancer, preferably an agent useful in treating or preventing a neurological disorder as otherwise described herein.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for inhibiting autophagy in a biological system, including a patient or subject according to the present invention.

Other compounds (identified in Table 1) were also found to be neuroprotective and useful for treatment of stroke and other neurological disorders. Neurological disorders include cerebral ischemia, de-myelinating conditions, and mechanical injury, as well as hypoxia-ischemia (stroke); head and spinal cord injury; epilepsy; schizophrenia; neurodegenerative disorders such as Alzheimer's disease, Parkinson's disease, Parkinsonism; Huntington's disease, Binswanger's disease, vascular cognitive impairment, vascular dementia, amyotrophic lateral sclerosis and multiple sclerosis; optic neuropathies such as glaucoma, light-induced retinal degeneration such as photoreceptor degeneration, and macular degeneration; disorders of photoreceptor degeneration such as retinitis pigmentosa; HIV-associated dementia (acquired immunodeficiency syndrome dementia complex) and HIV-associated neuropathy; metabolic, mitochondrial and infectious brain abnormalities such as, but not limited to, encephalitis; neuropathic pain syndromes such as causalgia or painful peripheral neuropathies; olivopontocerebellar atrophy; mitochondrial abnormalities and other biochemical disorders such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy; hepatic encephalopathy, Tourette's syndrome; drug addiction and drug dependency; drug withdrawal such as withdrawal from alcohol or opiates; and depression or anxiety syndromes.

All compounds identified herein as therapeutically useful may be administered in doses and dosage forms known to the art in therapeutically effective carriers and in the form of ions, pharmaceutically acceptable salts, and therapeutic isomers, enantiomers, analogs and homologs thereof.

Our cell-based system offers several advantages over brain slice-based high-throughput screening and is an effective method for identifying novel stroke drugs.

EXAMPLES

Materials and Methods
Primary Cortical Neurons Cultures

Cortical neurons were obtained from Spraque-Dawley rat embryos at day 18 of gestation. Cortices were triturated and pre-plated 4 times for 30 minutes in 150 mm vacuum-plasma treated dishes (BD). During these pre-plating steps, primarily non-neuronal cells adhere to the dish, thereby enriching the neuronal population. Enriched neurons were plated in Neurobasal medium containing 2% fetal bovine serum (FBS), 25 µM Glutamax, and penicillin-streptomycin (Gibco) in poly-D-lysine-coated white clear-bottomed 96-well plates or 24-well plates (Becton-Dickinson) at a density of $50 \times 10^3/cm^2$. Twenty-four hours later (1 day in vitro, 1 DIV), 50% of the medium was replaced with Neurobasal medium, 2% B27 (Gibco), and 4 µM cytosine arabinoside (AraC) (2 µM AraC final). At 5 DIV, 50% of the medium was replaced with Neurobasal, 2% B27. At 7 DIV, cortical cultures were 98% neurons as assessed by microtubule-associated protein 2 (MAP2) antibody labeling and flow cytometry analysis (data not shown). In vitro experiments were performed in quadruplicate and results are shown as means with standard deviation.

High-Throughput Oxygen-Glucose Deprivation Model of Stroke

The Prestwick Chemical Library (Prestwick Chemical) was screened for neuroprotection in OGD by pre-treating 7 DIV cortical neurons in 96-well dishes with 10 µM compounds for 30 minutes. All liquid handling was automated and performed by a Beckman Coulter Biomek NX multi-channel pipettor. The pretreatment medium was transferred to a clean plate for storage and was kept at 37° C. in a 5% $CO_2$ environment during the OGD exposure. After pretreatment, cells were washed 3 times with deoxygenated glucose-free Hank's buffered saline solution (HBSS), pH 7.4, to remove glucose and oxygen and were covered with 100 µl HBSS. HBSS was deoxygenated in a gas washing bottle with 60 liters of 95% nitrogen, 5% $CO_2$ per 250 ml HBSS. HBSS was maintained at 37° C. during deoxygenation in a water bath. Compounds were added to wells and plates were sealed with sealing tape and placed in a 37° C. incubator for 2 hours (OGD). After 2 hours, HBSS was removed and pretreatment medium was returned to the wells. After 24 hours, neuronal death was quantified using CytotoxGlo reagents (Promega) and a Victor[3] V luminometer (Perkin Elmer) according to the manufacturer's instructions. Eight wells per dish were used as DMSO-treated vehicle-only controls. For each dish, compounds producing a dead/live cell protease ratio 3 standard deviations below the average ratio of dead/live cell protease activity obtained with the vehicle were considered hits and underwent secondary screening.

Secondary Screening of Primary Hits

Neuroprotection by candidate compounds was assayed by measurement of apoptosis using terminal deoxynucleotidyl transferase dUTP nick end labeling (TUNEL) reagents as described previously.[6] At 7 DIV, primary neurons grown on poly-D-lysine-coated 22 mm-diameter cover slips in 24-well plates underwent 2 hours of OGD and were treated with a range of doses of each compound at reoxygenation. Compounds providing greater than 2-fold protection over vehicle were then administered at the optimal dose after OGD at intervals of 0, 15, 30, and 60 minutes post-reoxygenation.

Middle Cerebral Artery Occlusion (MCAO) Model

All animal procedures were approved by the University of New Mexico Institutional Animal Care and Use Committee and were in compliance with federal guidelines. Male spontaneously hypertensive rats (SHR) weighing 290-300 g were obtained from Charles River Laboratories. Animals were anesthetized with 2% isoflurane inhalant during all surgical procedures. The right common carotid artery (CCA) was ligated approximately 6 mm caudal to the bifurcation of the external and internal carotid arteries. With a vascular clamp in place on the CCA immediately caudal to the bifurcation, an incision was made in the CCA 5 mm caudal to the clamp and a nylon suture (Doccol Corporation) 30 mm in length with a 2-3 mm silicone coated tip (0.39 mm diameter) was advanced into the CCA lumen and secured in place with 2 4-0 silk sutures spaced 3 mm apart and tied loosely around the CCA caudal to the clamp. The clamp was removed and the suture advanced into the internal carotid artery until resistance was felt. In this position, the filament occludes the MCA origin and MCA territory becomes ischemic. The suture was secured with the 2 silk sutures around the CCA. The wound was closed and the animal was allowed to recover during the 90-minute occlusion period. After 90 minutes, the suture was removed and the CCA ligated rostral to the incision. At reperfusion, animals received 0.5 ml of vehicle (0.6% DMSO in normal saline) or 1 mg/kg isoxsuprine hydrochloride by IV injection through the lateral tail vein. All animals received 3 ml of subcutaneous saline after surgery to prevent dehydration. After 24 hours reperfusion, animals were sacrificed, brains were sectioned into 4 mm-thick quadrants, and infarcted tissue was identified by TTC staining. Edema-corrected infarct volume was calculated by subtracting the area of non-infarcted tissue in the ipsilateral hemisphere from the total volume of the contralateral hemisphere. Infarct volume was quantified using Image J software.

Statistical Analyses

Statistically significant differences between in vitro drug treatment groups were determined by one-way analysis of variance (ANOVA) with Bonferroni's multiple comparison test. Comparison of infarct volumes between animals receiving vehicle or isoxsuprine hydrochloride was performed using a two-tailed unpaired t-test. Differences between experimental groups were considered statistically significant if p<0.05 with a 95% confidence interval. All statistical analyses were performed using GraphPad Prism 5 software (GraphPad Software, Inc.)

Figure 2:
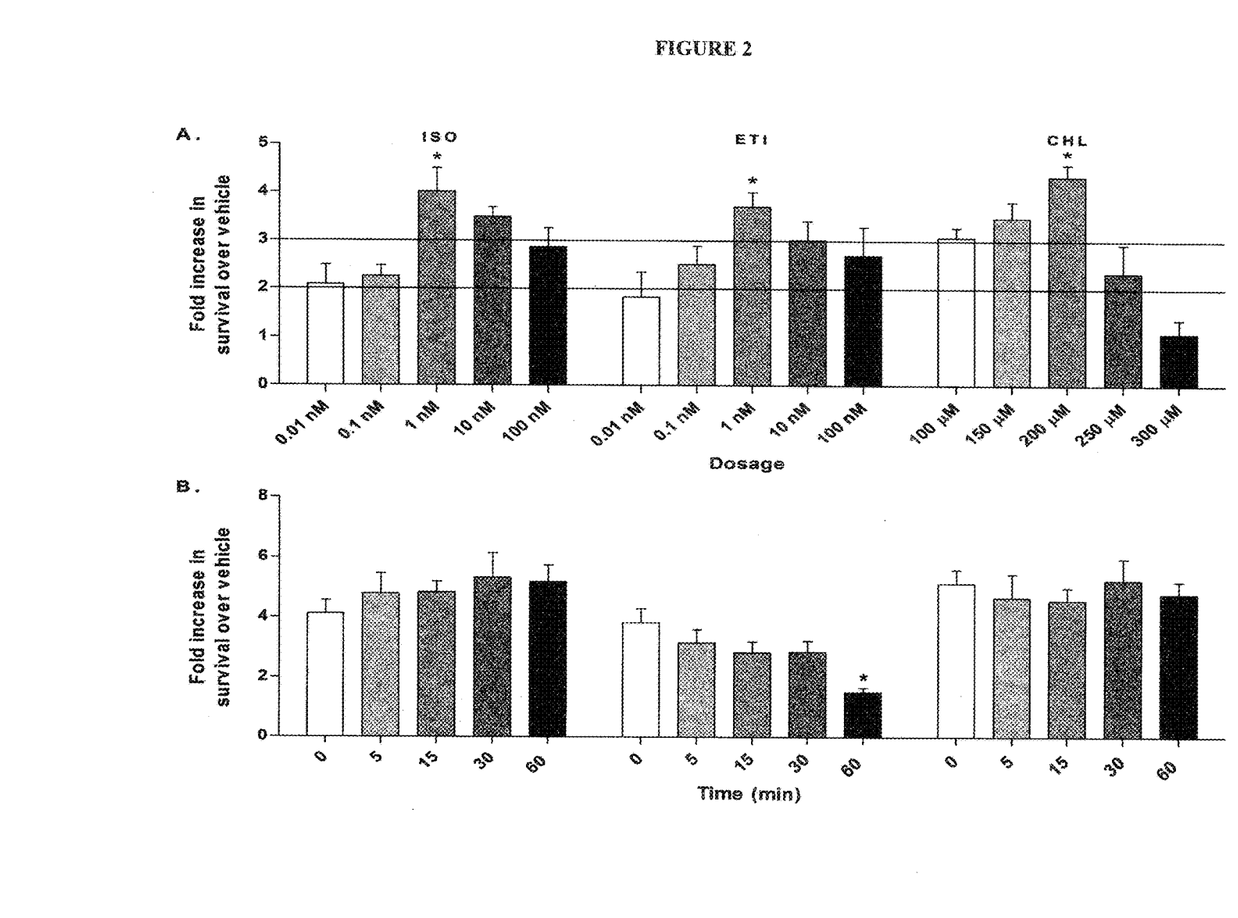

0, 15, 30, and 60 minutes after the onset of reoxygenation after 2 hours of OGD. Isoxsuprine and chlorphenesin carbamate demonstrated no loss of neuroprotection when administered up to an hour after reoxygenation while a significant decrease in neuroprotection by etilifrine was observed with treatment at 60 minutes (FIG. 2 B).

Isoxsuprine in an Animal Stroke Model

Figure 3:
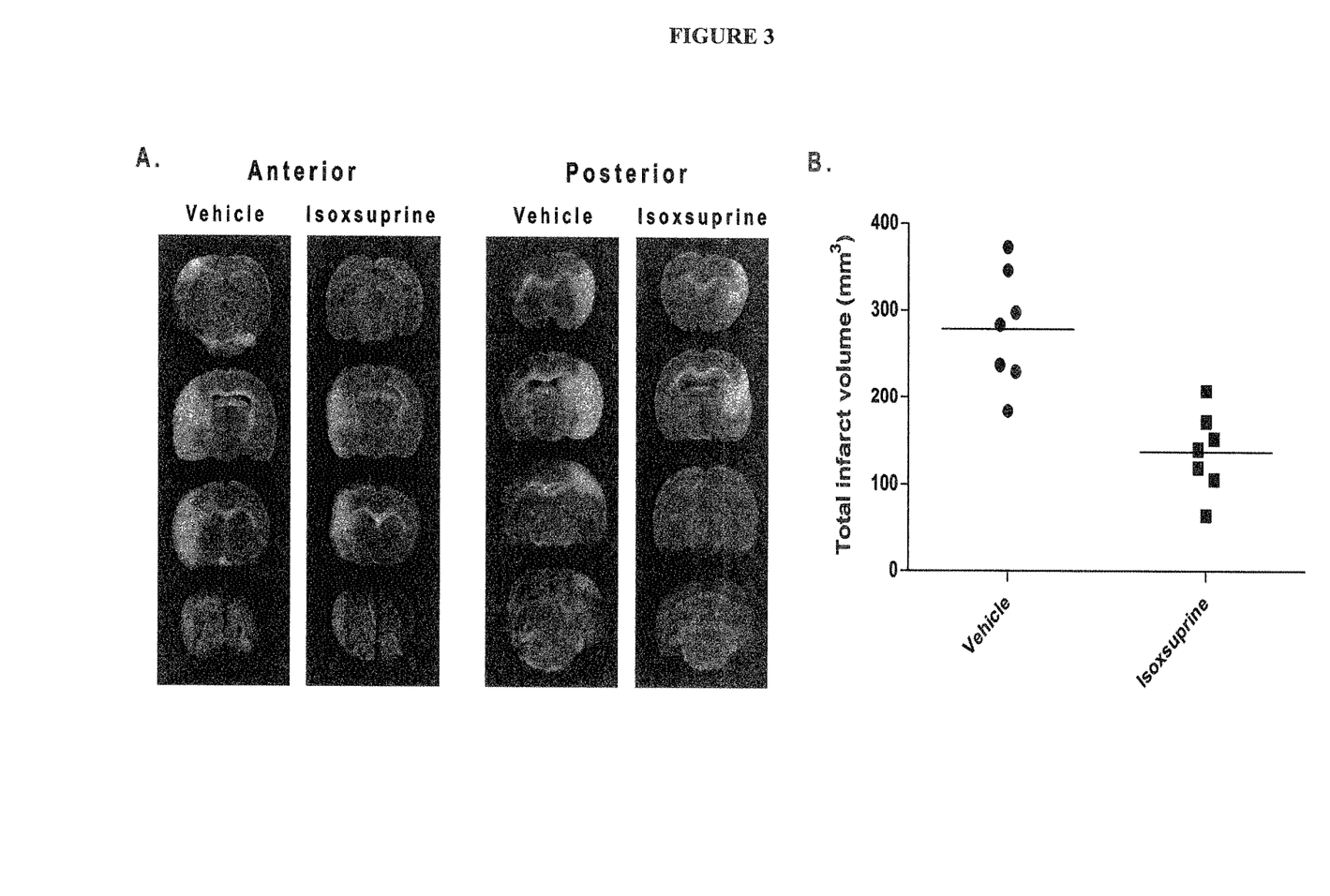
FIG. 3 illustrates the effect of isoxsuprine hydrochloride on infarct volume in an animal stroke model. A. Representative TTC-stained brain sections showing differences in infarction between animals receiving vehicle or isoxsuprine hydrochloride. B. Effect of isoxsuprine hydrochloride on infarct volume. Isoxsuprine hydrochloride (1 mg/kg, IV) given at the onset of reperfusion after a 90-minute MCAO significantly reduced infarct volume compared to vehicle alone (137±18 versus 279±25 mm$^3$, p<0.001). Closed circles, vehicle, closed squares, isoxsuprine hydrochloride, n=7 animals for each group.

To evaluate neuroprotection by isoxsuprine in vivo, 1 mg/kg isoxsuprine was administered by IV injection at reperfusion after a 90-minute occlusion of the right middle cerebral artery. Twenty-four hours after reperfusion onset, total edema-corrected infarct volume in the right hemisphere was calculated and compared between vehicle- and isoxsuprine-treated animals. Total infarct volume in vehicle-treated animals was 279±25 $mm^3$ compared to 137±18 $mm^3$ in isoxsuprine-treated animals (FIG. 3).

TABLE 1

Neuroprotective compounds identified through high-throughput screening of the Prestwick Chemical Library

| *     | Chemical name              | Therapeutic group | Mechanism of action                    |
|-------|----------------------------|-------------------|----------------------------------------|
| 5.567 | Dizocilpine maleate (MK-801)** | —             | Probe for NMDA receptors               |
| 5.130 | Mianserine hydrochloride   | Antidepressant    | 5-HT antagonist                        |
| 4.000 | Isoxsuprine hydrochloride  | Vasodilator       | β-adrenergic agonist                   |
| 3.800 | Meropenem                  | Antibacterial     | Peptidoglycan synthesis inhibitor      |
| 3.647 | Meclofenamic acid          | Antiinflammatory  | Cyclooxygenase inhibitor               |
| 3.540 | Guanabenz acetate**        | Antihypertensor   | Alpha agonist                          |
| 3.428 | Candesartan**              | Antihypertensive  | Angiotensin II receptor antagonist     |
| 3.400 | Etilefrine hydrochloride   | Vasoconstrictor   | Sympathomimetic                        |
| 3.270 | Haloperidol                | Antipsychotic     | Dopamine antagonist                    |
| 3.200 | Moxonidine                 | Antihypertensive  | Imidazoline receptor agonist           |
| 3.166 | Bumetanide**               | Diuretic          | Vascular cyclooxygenase activator      |
| 3.142 | Ibudilast**                | Antiinflammatory  | Phosphodiesterase inhibitor            |
| 3.117 | Chlorphenesin carbamate    | Muscle relaxant   | —                                      |
| 3.000 | Chicago sky blue 6B**      | —                 | Competitive glutamate uptake inhibitor |
| 3.000 | Prothionamide              | Antibacterial     | —                                      |
| 3.000 | Epitiostanol               | Antineoplastic    | —                                      |

* Standard deviations below dead/live cell protease ratio in DMSO vehicle-treated neurons.
**Compounds previously investigated in ischemic models.

Results

High-Throughput Screening

We identified 16 compounds which resulted in a dead/live cell protease ratio at least 3 standard deviations below vehicle-treated neurons 24 hours after OGD. Of these 16 compounds, 10 compounds have not been previously reported to have efficacy in models of ischemia and underwent secondary screening (Table 1).

Secondary Screening

Figure 1:
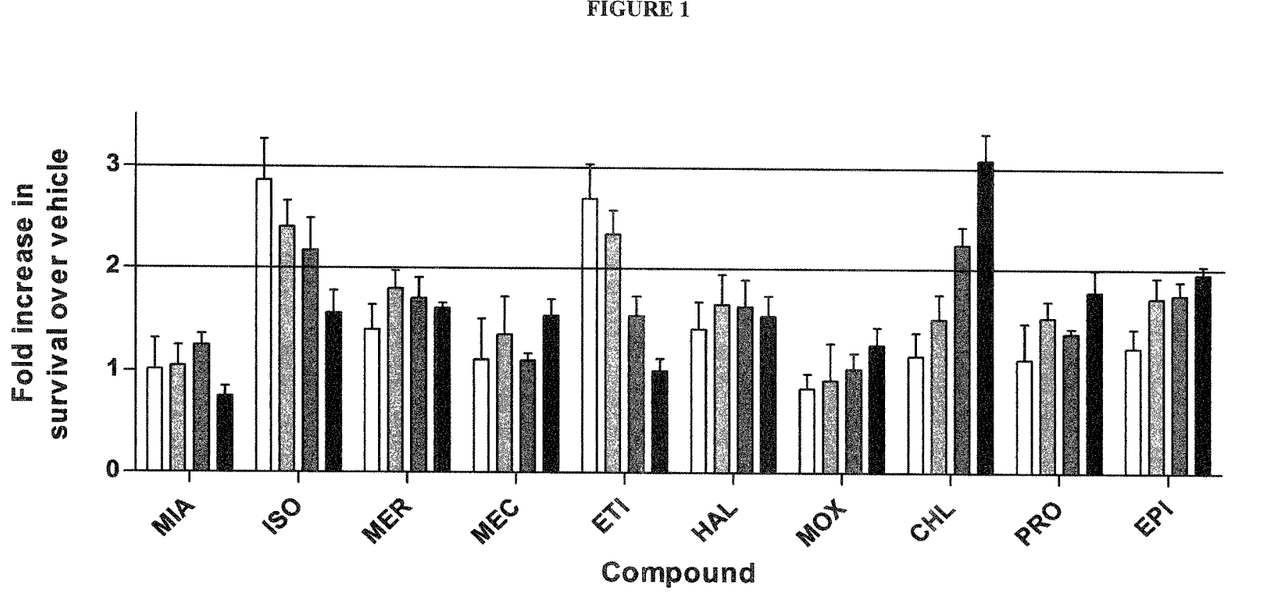
FIG. 1. Compounds identified through high-throughput screening administered at 0.1 (white), 1 (light gray), 10 (dark gray), and 100 μM (black) at reoxygenation after 2 hours OGD. Twenty-four hours later, cells survival was measured by TUNEL assay and compared to DMSO vehicle-treated neurons. Compounds providing at least 2-fold increased neuroprotection over vehicle were further investigated. MIA, mianserine hydrochloride, ISO, isoxsuprine hydrochloride, MER, meropenem, MEC, meclofenamic acid, ETI, etilifrine hydrochloride, HAL, haloperidol, MOX, moxonidine, CHL, chlorphenesin carbamate, PRO, prothionamide, EPI, epitiostanol.

The neuroprotective function of the 10 novel compounds identified in the high-throughput screening OGD model was evaluated using the TUNEL assay, a direct measure of apoptosis. In the secondary screen, compounds were administered at reoxygenation in doses ranging from 0.1 to 100 μM. Compounds providing at least a 2-fold increase in survival over vehicle included isoxsuprine hydrochloride, etilifrine hydrochloride, and chlorphenesin carbamate (FIG. 1). The optimal dose for these 3 compounds was determined by exposing neurons to 0.01 to 100 nM compound for isoxsuprine and etilifrine and 100 to 300 μM compound for chlorphenesin carbamate at reoxygenation. The doses providing maximum neuroprotection against OGD-induced apoptosis were 1 nM for isoxsuprine and etilifrine, and 200 μM for chlorphenesin carbamate (FIG. 2A). Using the optimal dose, compounds were then administered to neurons Discussion The goal of this study was to identify drugs with a history of human use which have novel therapeutic uses in the treatment of stroke and other neurological disorders. Utilizing a high-throughput OGD stroke model, we identified isoxsuprine hydrochloride a neuroprotectant and demonstrated efficacy of the molecule in an animal stroke model.

The OGD in vitro ischemia model has been used extensively in the identification and evaluation of potential stroke therapeutics. The ease of use and reproducibility of the system, along with lower cost of implementation contribute to its being amenable to preliminary experiments aiming to demonstrate biological activity of molecules before moving on to more costly and time consuming experiments in animal stroke models. OGD can be performed in organotypic brain slices, where the 3-dimensional arrangement of neurons, glial cells, and extracellular matrix is partially preserved, or in neuronal cultures which may consist of purified neurons, as in this study, or mixed populations of neurons, glial cells, and endothelial cells. While organtypic slices may most closely represent intact brain tissue, the method is labor- and time-intensive and expensive since numerous animals are required to manually prepare sufficient tissue sections needed to screen a chemical library which can contain thousands of compounds. Further, since multiple cell types are present, the establishment of neuron-specific cell death measures can be complex and complicates high-throughput screening efforts which typically benefit from rapid, easily implemented measures of cell survival.

In vivo, activation of glial cells and infiltration of immune cells at infarct sites during ischemia/reperfusion is believed to facilitate neuronal death. To approximate this situation, neurons can be co-cultured with astrocytes or microglia and subjected to OGD. In this mixed culture model, compounds that are neuroprotective can exert their effects through glial cells or directly on neurons. This latter activity can be verified by comparing neuroprotection by a compound during OGD in mixed cultures and in pure neurons. To examine direct neuroprotection by a compound, a pure neuronal population can be used. Use of an enriched neuronal population eliminates possible confounding effects introduced by the presence of glial cells, such as astrocytes and microglia, which are typically activated ex vivo and can influence neuronal survival and responses to stressors in ways not reflective of an in vivo ischemia/reperfusion scenario. Additionally, the primary neurons obtained from the embryonic pups of a single animal can be sufficient to screen an entire chemical library. Further, since only one cell type is present in enriched neurons, any cell death observed can be specifically attributed to neurons without performing additional experiments. These latter advantages particularly favor the use of pure neuronal populations in streamlined preliminary high-throughput screening studies.

Our cell-based model was validated by the identification of MK-801 as the top hit in a high-throughput screen, along with 5 other compounds with previously reported efficacy in ischemic models. MK-801 is a potent neuroprotectant and the highest affinity N-methyl-D-aspartate (NMDA) receptor antagonist known. Although highly protective in animal and in vitro ischemia models, MK-801 has a limited therapeutic window and causes severe neurological side effects, including psychosis. Pretreatment with compounds was used to validate the assay and increase sensitivity in the high-throughput screen. As our results show, the number 2 hit, mianserine hydrochloride, was highly protective when used as a pretreatment but ineffective when given at reoxygenation in the secondary screen. Similar results were reported with MK-801, which was neuroprotective during OGD when used as a pretreatment but significantly decreased in effectiveness when administered as few as 5 minutes after the onset of reoxygenation.[5] Thus, while pretreatment with compounds is reasonable during high-throughput screening, a secondary screen with compounds given at or after reoxygenation in vitro or reperfusion in vivo should be employed as pretreatment scenarios may not be clinically relevant to the treatment of acute stroke.

Our identification of isoxsuprine hydrochloride, a well-characterized $\beta_2$-adrenergic agonist and peripheral vasodilator, as a potent neuroprotectant in vitro and confirmation of its action in an animal stroke model suggest a significant effect of adrenergic receptor activation in promoting neuronal survival in ischemic stroke. This possibility is supported by several studies similarly demonstrating neuroprotection by $\beta$-agonists in animal and in vitro models of ischemia.[7-9] Clenbuterol, a $\beta_2$-adrenoreceptor agonist, is protective during OGD in mixed neuronal cultures and in animal stroke models. Clenbuterol is believed to exert neuroprotection by activating astrocytes and stimulating the production of nerve growth factors (NGFs) which promote neuronal survival.[8] Interestingly, clenbuterol is present in the Prestwick Chemical Library but was not identified as a neuroprotective compound in our high-throughput screening assay utilizing pure cortical neurons. This is consistent with the reported effects of clenbuterol on astrocyte-mediated NGF production. Thus, whether the "hits" emerging from a high-throughput screen target neurons, glial cells, or both can depend highly upon the in vitro OGD model utilized. Other studies have reported neuroprotective effects of $\beta$-adrenergic receptor blockade in animal models of ischemia.[10-12]

The disagreement between these findings is related to the choice and implementation of ischemic model as well differential selectivity of $\beta$-agonists and -antagonists employed for $\beta_1$-, $\beta_2$-, or both $\beta_1$- and $\beta_2$-adrenergic receptors. In some cell types, $\beta_1$- and $\beta_2$-adrenergic receptors can have opposing effects on apoptosis.[13] Evidence suggests that in vivo, the $\beta_2$-adrenergic receptor can be the major mediator of $\beta$-adrenergic agonist-associated neuroprotection.[9] Further, the growing realization that drugs with a sole known target can in fact exert biological activity in numerous pathways both underlies the current drug repurposing movement and explains the seemingly contradictory findings of neuroprotection by both $\beta$-agonists and antagonists.[14] There is clear and significant involvement of adrenergic receptor activation in neuronal survival decisions in ischemic injury.

Treatment with a single dose of isoxsuprine reduced infarct volume by half. This potent neuroprotective effect may be multifactorial in nature and may involve known biological effects of isoxsuprine and $\beta_2$-adrenergic agonists as well as yet uncharacterized off-target effects. Firstly, isoxsuprine is an effective peripheral vasodilator utilized in the treatment of cerebrovascular insufficiency. Administration of isoxsuprine can increase blood flow to the fragile penumbral region after ischemia and prevent evolution of the infarct core. Isoxsuprine possesses a significant $\alpha_1$-adrenoreceptor antagonist activity which can further enhance its potency as a smooth muscle relaxant and vasodilator.[15-16] Secondly, $\beta$-adrenergic receptor activation is known to depress brain inflammation.[17] Isoxsuprine can suppress the activation of microglia and production of inflammatory cytokines and chemokines which both promote leukocyte infiltration and can be directly neurotoxic.[18,19] Thirdly, isoxsuprine can induce glial cell-mediated NGF production and upregulate anti-apoptotic proteins such as Bcl-2 and Bcl-xl, similarly to other known neuroprotective $\beta_2$-agonists such as clenbuterol.[8,20] Fourthly, a direct protective effect on neurons can involve $\beta_2$-adrenergic receptor-mediated enhancement of neuronal production of calpastatin, an endogenous inhibitor of calpain which attenuates apoptosis.[21] Lastly, isoxsuprine is a NR2B-selective NMDA receptor antagonist[22] and can prevent neuronal excitotoxicity in stroke and neurological disorders described herein.

In summary, our results validate a novel, robust, and inexpensive cell-based OGD model for the identification of potential therapeutics for stroke and neurological disorders through high-throughput screening of chemical libraries. We demonstrate that isoxsuprine hydrochloride is a potent neuroprotectant for the treatment of stroke and neurological disorders.

All publications referred to or listed herein are incorporated herein by reference to the extent not inconsistent herewith for purposes of enablement and written description.

Although the inventions disclosed herein have been illustrated using specific examples, it will be understood that method steps and conditions, reagents, and other specific compounds equivalent to those specifically disclosed should be considered to be covered by the claims hereof.

REFERENCES

1. Go A S, Mozaffarian D, Roger V L, et al. American Heart Association Statistics Committee and Stroke Statistics Subcommittee. Heart disease and stroke statistics—2013 update: a report from the American Heart Association. Circulation. 2013; 127:e6-e245.
2. Eissa A, Krass I, Bajorek B V. Optimizing the management of acute ischaemic stroke: a review of the utilization of intravenous recombinant tissue plasminogen activator (tPA). J Clin Pharm Ther. 2012; 37:620-9.
3. Chong C R, Sullivan D J Jr. New uses for old drugs. Nature. 2007; 448:645-6.
4. Allison M. NCATS launches drug repurposing program. Nat Biotechnol. 2012; 30:571-2.
5. Wang J K, Portbury S, Thomas M B, Barney S, Ricca D J, Morris D L, Warner D S, Lo D C. Cardiac glycosides provide neuroprotection against ischemic stroke: discovery by a brain slice-based compound screening platform. Proc Natl Acad Sci USA. 2006; 103:10461-6.
6. Hill J W, Poddar R, Thompson J F, Rosenberg G A, Yang Y. Intranuclear matrix metalloproteinases promote DNA damage and apoptosis induced by oxygen-glucose deprivation in neurons. Neuroscience. 2012; 220:277-90.
7. Semkova I, Schilling M, Henrich-Noack P, Rami A, Krieglstein J. Clenbuterol protects mouse cerebral cortex and rat hippocampus from ischemic damage and attenuates glutamate neurotoxicity in cultured hippocampal neurons by induction of NGF. Brain Res. 1996; 717:44-54.
8. Culmsee C, Semkova I, Krieglstein J. NGF mediates the neuroprotective effect of the beta2-adrenoceptor agonist clenbuterol in vitro and in vivo: evidence from an NGF-antisense study. Neurochem Int. 1999; 35:47-57.
9. Junker V, Becker A, Hühne R, Zembatov M, Ravati A, Culmsee C, Krieglstein J. Stimulation of beta-adrenoceptors activates astrocytes and provides neuroprotection. Eur J Pharmacol. 2002; 446:25-36.
10. Savitz S I, Erhardt J A, Anthony J V, Gupta G, Li X, Barone F C, Rosenbaum D M. The novel beta-blocker, carvedilol, provides neuroprotection in transient focal stroke. J Cereb Blood Flow Metab. 2000; 20:1197-204.
11. Amory D W, Grigore A, Amory J K, Gerhardt M A, White W D, Smith P K, Schwinn D A, Reves J G, Newman M F. Neuroprotection is associated with beta-adrenergic receptor antagonists during cardiac surgery: evidence from 2,575 patients. J Cardiothorac Vasc Anesth. 2002; 16:270-7.
12. Goyagi T, Kimura T, Nishikawa T, Tobe Y, Masaki Y. Beta-adrenoreceptor antagonists attenuate brain injury after transient focal ischemia in rats. Anesth Analg. 2006; 103:658-63.
13. Zhu W Z, Zheng M, Koch W J, Lefkowitz R J, Kobilka B K, Xiao R P. Dual modulation of cell survival and cell death by beta(2)-adrenergic signaling in adult mouse cardiac myocytes. Proc Natl Acad Sci USA. 2001; 98:1607-12.
14. Medina-Franco J L, Giulianotti M A, Welmaker G S, Houghten R A. Shifting from the single to the multitarget paradigm in drug discovery. Drug Discov Today. 2013; 18:495-501.
15. Elliott J, Soydan J. Characterisation of beta-adrenoceptors in equine digital veins: implications of the modes of vasodilatory action of isoxsuprine. Equine Vet J Suppl. 1995; 19:101-7.
16. Belloli C, Carcano R, Arioli F, Beretta C. Affinity of isoxsuprine for adrenoreceptors in equine digital artery and implications for vasodilatory action. Equine Vet J. 2000; 32:119-24.
17. Markus T, Hansson S R, Cronberg T, Cilio C, Wieloch T, Ley D. β-Adrenoceptor activation depresses brain inflammation and is neuroprotective in lipopolysaccharide-induced sensitization to oxygen-glucose deprivation in organotypic hippocampal slices. J Neuroinflammation. 2010; 7:94.
18. De Paola M, Buanne P, Biordi L, Bertini R, Ghezzi P, Mennini T. Chemokine MIP-2/CXCL2, acting on CXCR2, induces motor neuron death in primary cultures. Neuroimmunomodulation. 2007; 14:310-6.
19. Thirumangalakudi L, Yin L, Rao H V, Grammas P. IL-8 induces expression of matrixmetalloproteinases, cell cycle and pro-apoptotic proteins, and cell death in cultured neurons. J Alzheimers Dis. 2007; 11:305-11.
20. Zhu Y, Prehn J H, Culmsee C, Krieglstein J. The beta2-adrenoceptor agonist clenbuterol modulates Bcl-2, Bcl-xl and Bax protein expression following transient forebrain ischemia. Neuroscience. 1999; 90:1255-63.
21. Rami A, Volkmann T, Agarwal R, Schoninger S, Nürnberger F, Saido T C, Winckler J. beta2-Adrenergic receptor responsiveness of the calpain-calpastatin system and attenuation of neuronal death in rat hippocampus after transient global ischemia. Neurosci Res. 2003; 47:373-82.
22. Whittemore E R, Ilyin V T, Woodward R M. Subtype-selective antagonism of NMDA receptors by Nylidrin. Soc Neurosci Abst. 1996; 22:506-507.
US Patent Publication No. 20080139614
US Patent Publication No. 20070123556
US Patent Publication No. 20120003180
U.S. Pat. No. 7,618,615

What is claimed is:

1. A method of treating or preventing an ischemic or hemorrhagic stroke or transient ischemic attack (TIA) in a subject in need comprising administering to said subject from 0.001 to 1.0 mg/kg of isoxsuprine or a pharmaceutically acceptable salt, analog or derivative thereof, wherein said isoxsuprine or a pharmaceutically acceptable salt, analog or derivative thereof is administered initially to the subject within about 15-30 minutes to about 12 hours after the subject expresses one or more symptoms of a stroke or TIA and is thereafter administered at every sixty to ninety minutes for six hours or until the subject is asymptomatic.

2. The method of claim 1, wherein said isoxsuprine or a pharmaceutically acceptable salt, analog or derivative thereof is administered intravenously.

3. The method of claim 1, wherein said isoxsuprine or a pharmaceutically acceptable salt, analog or derivative thereof is administered to the subject intravenously after the subject expresses an occlusion of a cerebral artery.

4. The method of claim 1, wherein said isoxsuprine or a pharmaceutically acceptable salt, analog or derivative thereof is administered to the subject intravenously after the onset of reperfusion of an occluded cerebral artery.

5. The method of claim 1, wherein the subject is treated concomitantly with one or more compositions selected from the group consisting of a thrombolytic agent, an anti-inflammatory agent, an immunosuppressant, an antioxidant, an α- or β-adrenergic agonist or antagonist and a NMDA receptor antagonist.

6. A method of treating or preventing an ischemic or hemorrhagic stroke or transient ischemic attack (TIA) in a subject in need comprising administering to said subject from 0.001 to 1.0 mg/kg of isoxsuprine or a pharmaceutically acceptable salt, analog or derivative thereof, wherein said isoxsuprine or a pharmaceutically acceptable salt, analog or derivative thereof is administered intravenously at the onset of reperfusion of an occluded cerebral artery.

7. A method of protecting neuronal cells from ischemia- or hypoxia-induced cell death in a subject in need thereof comprising administering to said subject a therapeutically effective amount of at least one agent selected from the group consisting of isoxsuprine, chlorphenesin or a pharmaceutically acceptable salt, analog or derivative thereof, wherein said agent is administered to the subject at around 15-30 minutes to about 12 hours after the subject expresses an occlusion of a cerebral artery, or at the onset or after the onset of reperfusion of an occluded cerebral artery.

8. The method of claim 7, wherein said agent is administered to the subject intravenously after the onset of reperfusion of an occluded cerebral artery.

9. The method of claim 7, wherein said agent is administered intravenously at the onset of reperfusion of an occluded artery.

10. The method of claim 7, wherein said agent is administered intravenously after the subject expresses an occlusion of a cerebral artery.

11. A method of treating or preventing reperfusion injury comprising administering to a subject in need thereof a therapeutically effective amount of at least one agent selected from the group consisting of isoxsuprine, chlorphenesin or a pharmaceutically acceptable salt, analog or derivatives thereof, wherein the subject is at risk of suffering, or is suffering from, or has suffered focal cerebral ischemia or global cerebral ischemia and said agent is administered intravenously at the onset of reperfusion of an occluded cerebral artery.

* * * * *